United States Patent [19]

Ballmann et al.

[11] Patent Number: 4,550,856
[45] Date of Patent: Nov. 5, 1985

[54] FACE MASK AND DISPENSER ASSEMBLY

[76] Inventors: Fred A. Ballmann, 12051 W. 100th St., Lenexa, Kans. 66215; James M. Cooper, 6011 W. 61st Ter., Shawnee Mission, Kans. 66202

[21] Appl. No.: 584,742

[22] Filed: Feb. 29, 1984

[51] Int. Cl.⁴ ............................................. B65H 1/00
[52] U.S. Cl. ..................................... 221/63; 221/283; 221/307; 128/202.13
[58] Field of Search ................. 221/303, 307, 310, 63, 221/283, 240, 305, 306, 308, 312 C; 2/9; 128/206.19, 202.13; 206/499

[56]            References Cited
            U.S. PATENT DOCUMENTS

| | | | |
|---|---|---|---|
| 1,116,399 | 11/1914 | Elsas | 221/63 |
| 1,346,792 | 7/1920 | Bergman | 221/310 |
| 1,752,607 | 4/1930 | Miller | 221/63 |
| 2,115,923 | 5/1938 | Cooper | 221/63 |
| 3,220,409 | 11/1965 | Liloia et al. | 2/9 |
| 3,435,988 | 4/1969 | Jonas et al. | 221/310 |
| 3,488,772 | 1/1970 | Sturm | 2/9 |

Primary Examiner—H. Grant Skaggs

[57] ABSTRACT

A compact dispensing device, especially useful in conjunction with disposable face masks, is provided which serves to store such masks and to serially dispense the masks in response to user demand. The dispenser preferably includes an elongated container in which the masks are stored and an apertured retainer secured across one end of the container. The retainer preferably presents a depending, inwardly converging sidewall around the aperture and the masks are interfitted such that the strap of the mask adjacent the retainer is positioned through the retainer aperture. The retainer aperture presents the same irregular cross-sectional configuration as the mask cross-section, with the masks being serially dispensed by simply pulling on the strap of the mask presented through the retainer aperture. In preferred forms, the depending sidewall has an inwardly-extending lip with the wall and lip cooperating to allow the masks to be singularly dispensed while retaining the remaining masks within the container.

12 Claims, 16 Drawing Figures

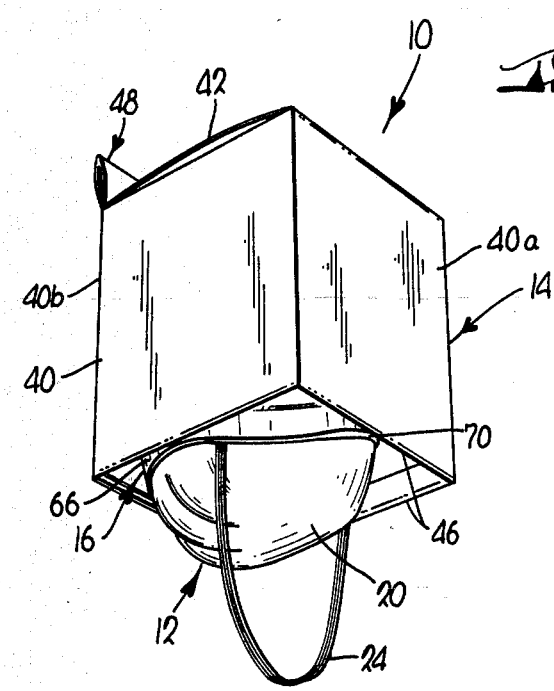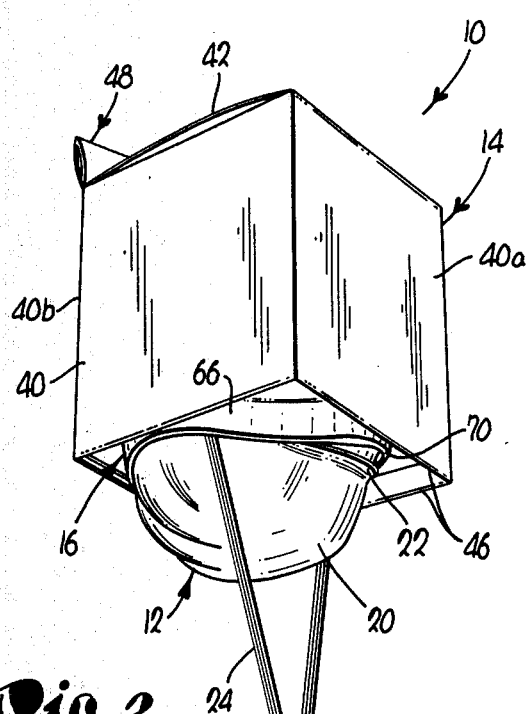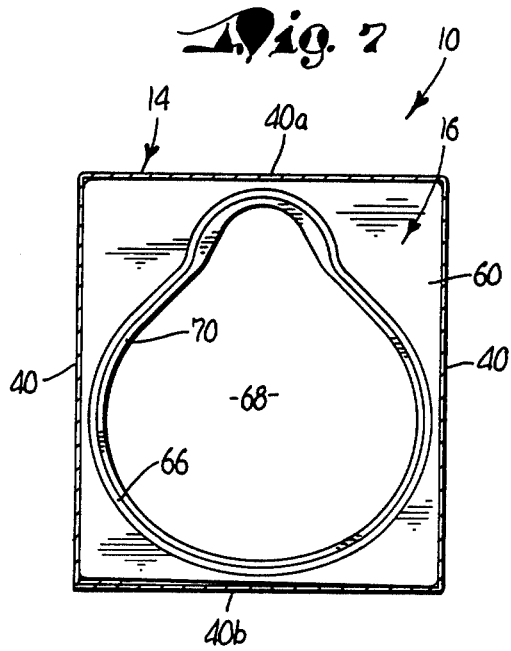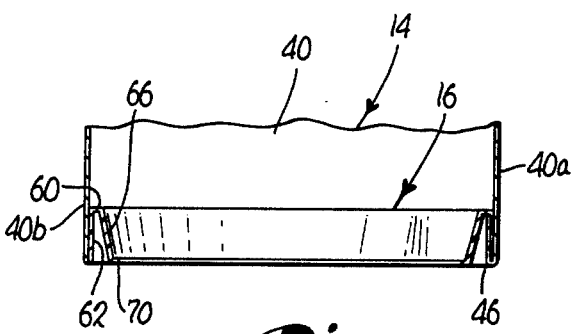

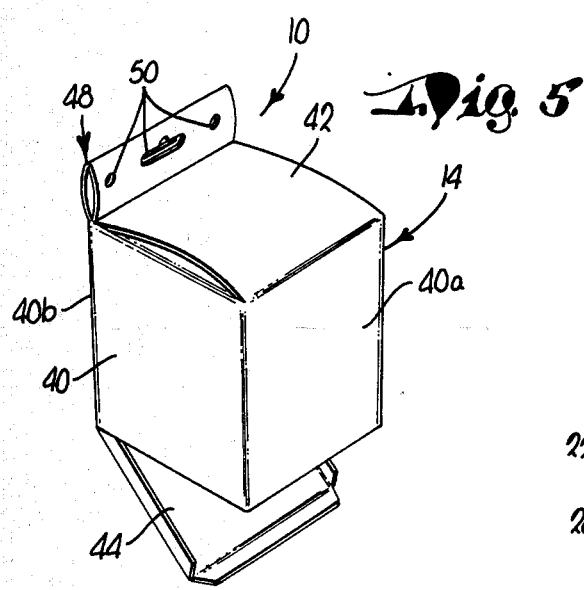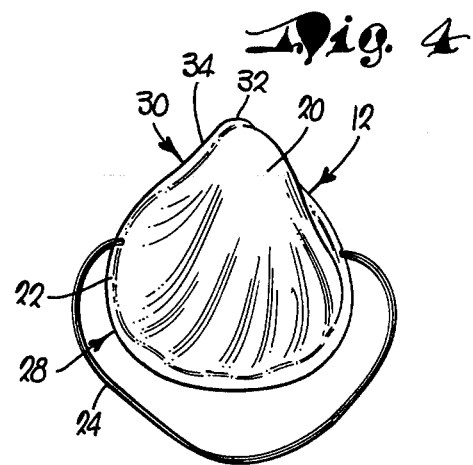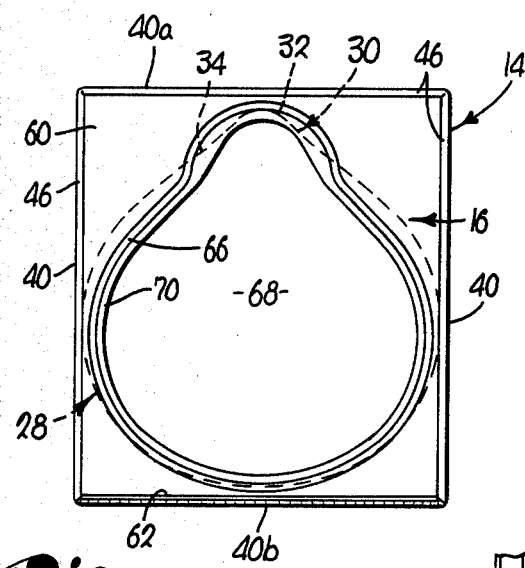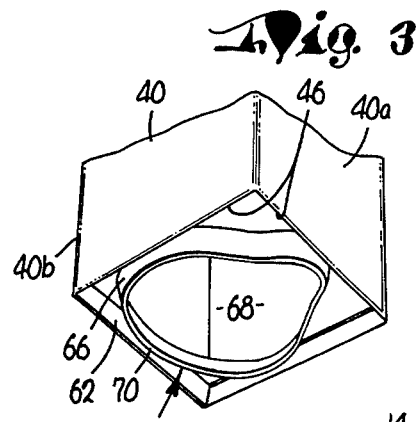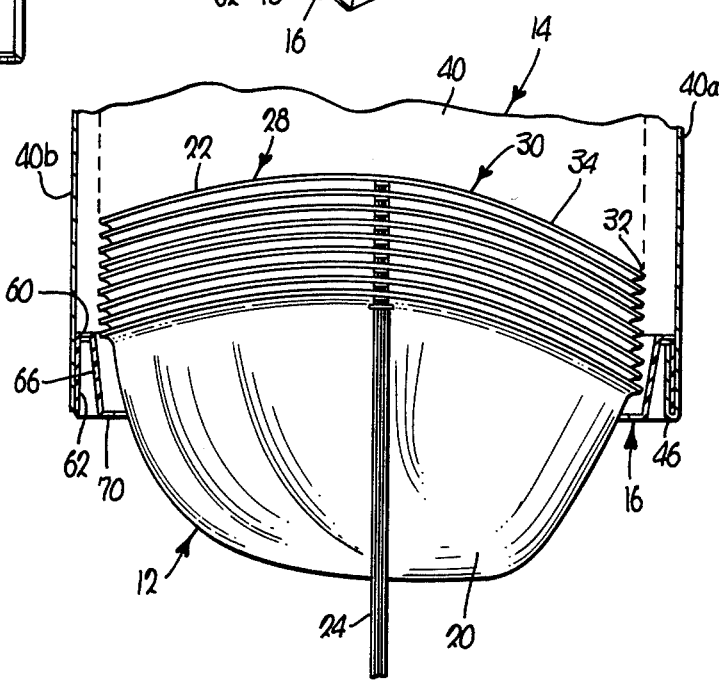

FACE MASK AND DISPENSER ASSEMBLY

BACKGROUND OF THE INVENTION

1. Field of the Invention

This invention relates to a face mask dispenser for efficiently storing such masks and which serially dispenses the masks in response to user demand. More particularly, it is concerned with a face mask dispenser comprising an elongated container and an apertured retainer disposed across one end of the container, with the retainer particularly constructed for serially dispensing the face masks presented to the retainer.

2. Description of the Prior Art

Particular types of dispensers are known and have enjoyed widespread use in serially dispensing such diverse items as paper cups, paper towels, facial tissue, etc. When the item to be dispensed is low cost and disposable, it is important to be able to dispense such items inexpensively without damage to the product. Most often, such dispensers have been concerned with items having a regular cross-section, which greatly simplifies the design and construction of the dispenser itself. For example, paper cups have a circular cross-section, which allows a dispenser to be easily designed and constructed.

Face masks, particularly disposable face masks, are being used more frequently in response to a recognition that inhalation of a large amount of particulates can be harmful to the health. Thus, people encountering a work environment in which a large number of particles are encountered in the air have found it helpful to use a face mask to protect against inhalation of such particles. For example, the user might wear a face mask when performing such tasks as farming field operations, woodworking, sweeping, or painting. While face masks have been designed which are helpful in such work conditions, it has heretofore been inconvenient to access such disposable face masks for use. Owing perhaps to the irregular cross-section of such disposable face masks, there has not been a convenient way to obtain such a face mask. That is, heretofore such masks have been shipped and stored in a box and accessed for use by unpacking the box. Thus, a significant advance in the art would be made if a compact dispenser of simple design were devised which serially dispensed a face mask in response to user demand.

SUMMARY OF THE INVENTION

In response to such a need, the dispensing device in accordance with the present invention is effective in not only providing a compact storage container for storing a number of such face masks, but additionally allows the face masks to be serially dispensed in accordance with user demand. That is to say, the dispensing device of the present invention provides ready access to the masks stored therein. Using the present invention, a user can obtain a mask for wear by simply pulling on the strap of a mask, with the dispensing device retaining the remaining face masks for later use.

The present invention broadly presents a container for providing a storage area for a plurality of face masks in serially stacked relationship and a retainer disposed in the container for normally retaining the masks and operable to allow the masks to be serially dispensed in response to the user pulling on a respective mask strap in a downward direction. To this end, the retainer advantageously has an aperture having an irregular configuration similar to the mask cross-section. The masks are positioned in the container such that the strap of the lowermost mask is presented through the aperture with the retainer preventing removal of the masks from the container. In preferred forms, the retainer includes a wall structure depending from the retainer around the aperture and inwardly converging to cooperate in retaining the mask in the container. In particularly preferred forms, an inwardly-extending lip is presented at the distal end of the depending wall structure. Thus, use of the dispensing device of the present invention is a matter of simply pulling on the mask strap presented through the aperture, with the retainer dispensing the mask adjacent the insert, while retaining the remaining mask within the container.

BRIEF DESCRIPTION OF THE DRAWING

FIG. 1 is a perspective view of the dispensing device in accordance with the present invention, and illustrates a face mask positioned for dispensing;

FIG. 2 is a perspective view similar to FIG. 1 and illustrates a user pulling on the strap of a face mask to show the method of dispensing;

FIG. 3 is a fragmentary perspective view of the retainer disposed at one end of the container of the present invention;

FIG. 4 is a perspective view of a face mask typical of such masks dispensed by the present invention;

FIG. 5 is a perspective view of the dispensing device of the present invention and illustrates the tear-away bottom cover of the container and the hangup tab for mounting the container on a wall;

FIG. 6 is a bottom plan view of the retainer of the present invention and particularly illustrates the inwardly-converging depending wall and the inwardly-extending lip, and depicts in phantom the general outline of a face mask overlying the retainer;

FIG. 7 is a top plan view of the retainer of the present invention with the container in section;

FIG. 8 is a fragmentary, sectional view depicting the retainer of the present invention;

FIG. 9 is a fragmentary view with the retainer and container of the present invention in section and showing an elevation of the innerfitted face mask stored in the dispensing device hereof;

DESCRIPTION OF THE PREFERRED EMBODIMENT

Figure 10:
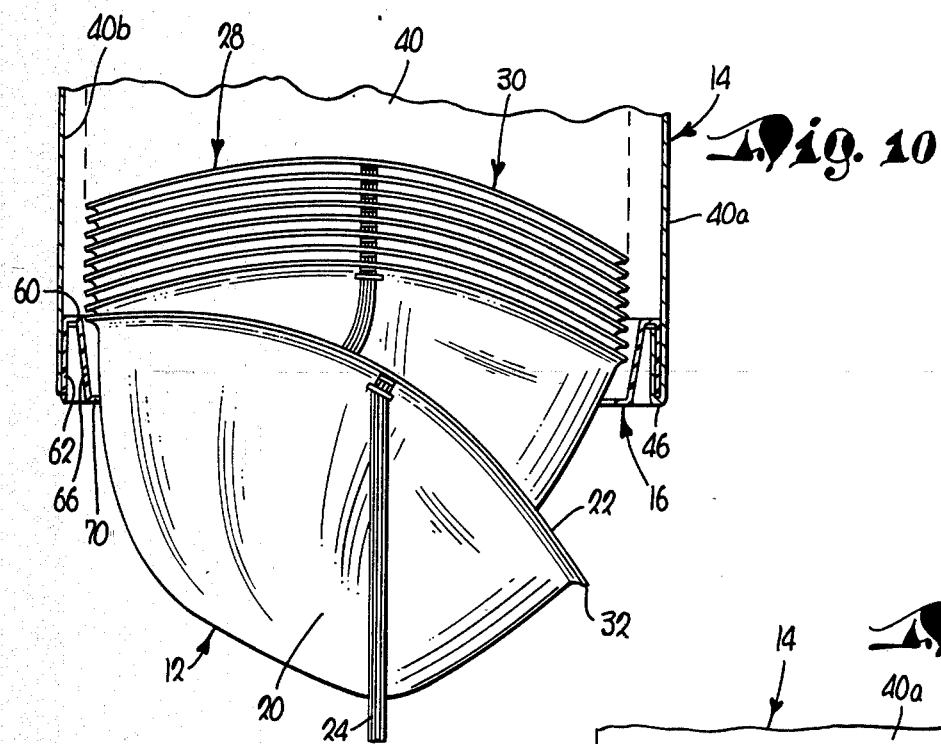
FIG. 10 is a fragmentary view similar to FIG. 9 and illustrates the initial dispensing movement of a mask.

Referring now to the drawing particularly FIGS. 1–12, a device 10 for storing and dispensing a plurality of face masks 12 is illustrated, and broadly includes container means 14 configured for providing a storage area for the masks 12 and retainer means 16 disposed in the container means 14 for normally retaining the masks 12 and operable to allow the masks 12 to be serially dispensed from the container 14. The face masks 12 have a cross-section presenting an irregular periphery and are preferably interfitted in stacked relationship in container 14. The masks 12 illustrated in the drawing for use in the preferred embodiment each present a lowermost cup defining surface 20, an uppermost peripheral, face-engaging flange 22 and an elastic strap 24 secured to the marginal edges of the face mask adjacent the flange 22 as shown in FIG. 4. Generally speaking, the mask 12 has a certain cross-section 26 taken adjacent the flange 22 and as shown in phantom in FIG. 6, the cross-section 26 presents a generally circular mouth-receiving region 28 adjoining a generally parabolic, nose-receiving region 30. As can be appreciated viewing FIGS. 4, 6, the nose-receiving region 30 presents an apex, bridge-of-the-nose section 32 and a pair of converging side sections 34 on either side of the apex section 32. Preferably, the strap 24 is secured to the mask 12 so that the nose region 30 emerges first in dispensing operation. To this end, with a centroidal axis of mass defined along the prolate portion of mouth-receiving region 28 adjacent flange 22, the strap 24 is secured between the controidal axis and nose-receiving region 30.

The container means 14 presents four generally planar, interconnected sidewalls 40 in a box-like configuration, a generally planar top 42 enclosing the sidewalls 40 at one end, and a generally planar bottom 44 enclosing the sidewalls 40 at the other end. Advantageously, the top 42 and bottom 44 are each hingedly connected to one of the sidewalls 40 along a marginal adjoining edge. Thus, viewing FIG. 5, the top 42 is hingedly connected to the front sidewall 40a, while the bottom 44 is hingedly connected to the back sidewall 40b. Preferably, the connection edge between the bottom 44 and the sidewall 40b is perforated such that the bottom 44 can be torn away from the container 14 and disposed of (compare FIGS. 5 and 1). Further, container 14 includes an attachment structure 48 apertured as at 50, and secured to the sidewall 40b adjacent the top 42 for hanging the device 10.

The retainer means 16 of the preferred embodiment includes a generally planar, rectangularly configured, engagement surface 60 and four depending attachment elements 62 along the marginal edges of the engagement surface 60 (see FIGS. 6-8). As more clearly shown in FIGS. 6, 8, the retainer 16 is secured to the container 14 by disposing the retainer 16 in the container 14 adjacent the bottom 44 such that the attachment elements 62 engage the interior faces of the sidewalls 40. The cusp portion 46 of the sidewalls 40 are bent back into engagement with the attachment elements 62 and the attachment elements 62 are secured by suitable means (such as staples, and/or glue not shown). As shown in FIG. 6, cusp portions 46 are present in only three out of the four sidewalls 40 with the remaining sidewall 40b providing the hinged, perforated interconnection to the bottom 44 and thus not presenting a cusp portion 46.

Centrally located in the engagement surface 60 is a depending wall structure 66 which defines an aperture 68 through the retainer 16. Preferably, the wall structure 66 inwardly converges and terminates at its distal end to present an inwardly-extending lip 70 (see for example, FIGS. 6-8). It should be understood that the general configuration of the wall structure 66 and aperture 68 are similar to the one cross-section 26 of mask 12 and thus, each presents a generally circular mouth-receiving region and a generally parabolic nose-receiving region, with the nose-receiving region presenting an apex section and side sections.

In the preferred embodiment, the dimensions of the retainer 16 have been found to be preferably interrelated with the dimensions of the mask 12. Thus, the dimensions of the uppermost portion of the wall structure 66 adjacent the engagement surface 60 presents a cross-section approximately equal to the outermost periphery of the flange 22 of the mask 12 (see FIG. 6). The lowermost, inwardly-converging portions of the wall structure 66 preferably are configured to present a cross-section such that the flange 22 of the mask 12 engages the wall structure 66 to normally prevent passage of the mask 12 through the aperture 68 (see FIGS. 9-12). Similarly, the lip 70 extends inwardly from the wall structure 66 to present a further reduction in the effective size of the aperture 68 as more clearly shown in FIG. 7. It has been found that in the preferred design, the dimension of the portion of the lip 70 in the mouth-receiving region is generally uniform, while in the nose-receiving region, the lip 70 is dimensioned such that the side sections extend further inwardly than does the apex section.

Figure 13:
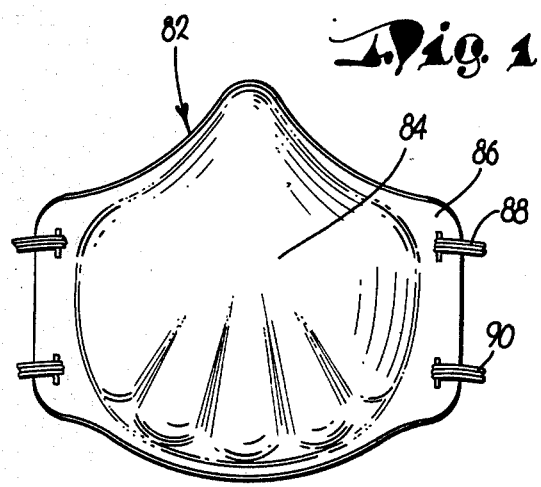
FIG. 13 is an elevatioinal view of another type of face mask stored and dispensed by the present invention.
Figure 14:
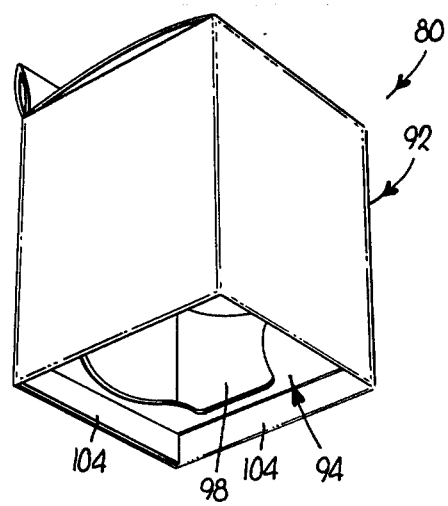
FIG. 14 is a perspective view of an alternative embodiment of the present invention.
Figure 15:
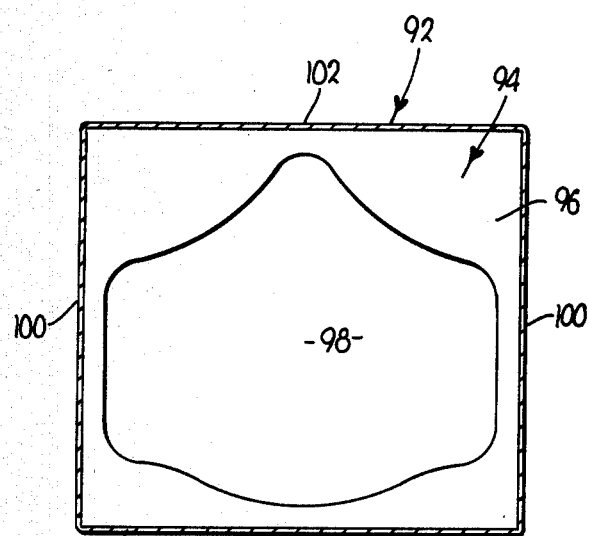
FIG. 15 is a sectional view of the retainer used in the alternative embodiment.
Figure 16:
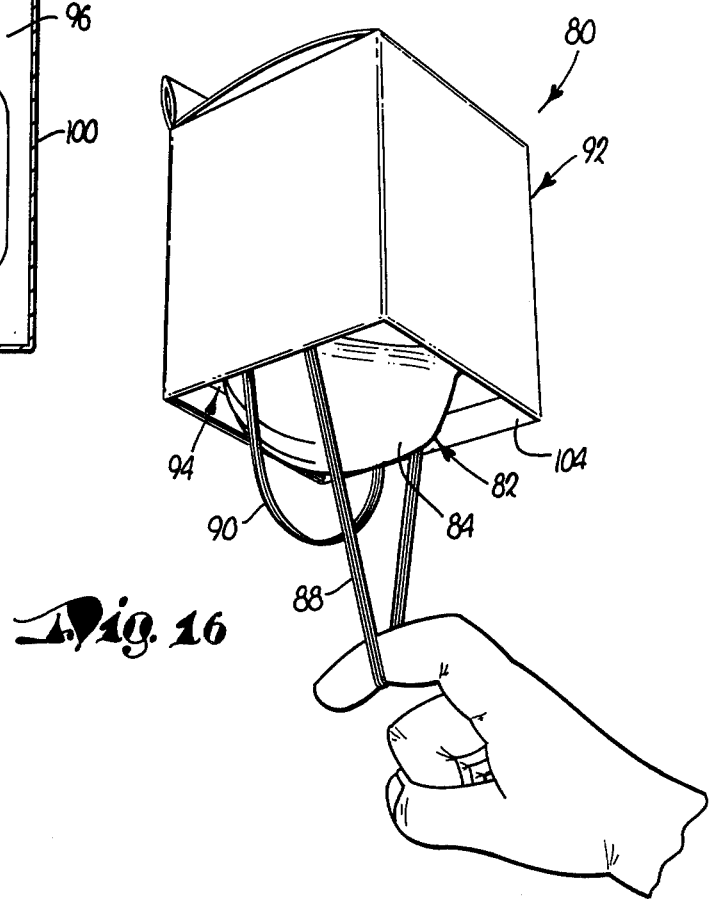
FIG. 16 is a perspective view similar to FIG. 2 and depicting the dispensing operation of the mask shown in FIG. 13 from the alternative embodiment of the present invention.

Turning now to FIGS. 13-16, the alternative embodiment of the present invention is illustrated, and includes a device 80 for dispensing a plurality of interfitted face mask 82. The mask 82 illustrated in FIG. 13 is similar to the mask illustrated in FIG. 4 and includes a cup surface 84, a flange surface 86 extending outwardly from the cup surface 84, and a pair of elastic straps 88, 90 having their respective distal ends secured to the flange 86. It should be understood that either of the face masks 12, 82, may be dispensed from either the preferred embodiment 10 or alternative embodiment 80; the mask 82 in FIG. 13 simply illustrates that different types of masks may be dispensed in accordance with the present invention. As shown in FIGS. 14-16, the device 80 presents a container means 92 and a retainer means 94, with the container means 92 being substantially identical to the container means 14 of the preferred embodiment. The retainer 94 is preferably fabricated from the same material as the container means 92 (for example, cardboard). The retainer 94 simply presents a generally planar engagement surface 96 defining an aperture 98 therein. The engagement surface 96 has three flaps 100 connected to the marginal edges thereof, with a fourth flap 102 secured to both the engagement surface 96 and container means 92. The container 92 presents three cusp portions 104 along the lowermost surfaces thereof, such that the retainer 94 is secured in the container 92 with the flaps 100, 102 engaging the interior of the container means 92, and the three cusp portions 104 bent inwardly and upwardly to engage flaps 100. The cusp portions are secured in place by suitable means (such as staples, and/or glue not shown).

In use, the dispensing device 10 is designed to provide a storage container for the masks 12 as well as serially dispense the masks 12 in response to user demand. Although the device 10 might be constructed as a permanent dispensing device, the preferred embodiment of the device 10 is constructed to be disposable after depletion of the mask supply. Thus, the masks 12 are packed into the container 14 at the factory with the bottom 44 and top 42 secured in sealing engagement with the sidewalls 40. This allows the container 14 to be used as the shipping compartment, the display package for retail sale, and to serve as the storage container and dispenser by the user. Typically, the user would take the device 10 and secure it to a wall in his shop or other convenient location, by simply retaining one of the apertures 50 over a hook on the wall. The user then would have the option of tearing the bottom 44 off the container 14 thereby exposing a mask 12 adjacent the retainer 16 as shown in FIGS. 1 and 9, or leave the bottom 44 in tact, allowing for future closure.

The masks are packed at the factory in a innerfitted relationship such that the strap 24 of the next succeeding masks is received in the cup 20 of the preceding mask. As shown in FIG. 9, the masks are then stacked with the cup surface 20 oriented towards the retainer 16 and the straps 24 disposed towards the aperture 68. With the bottom 44 torn away from the container 14 or with the bottom 44 hanging downward and the device 10 upright, the strap 24 of the mask 12 adjacent the retainer 16 hangs downwardly from the aperture 68, with portions of the retainer 16 engaging portions of the masks 12 to retain the masks 12 within the container 14.

Figure 11:
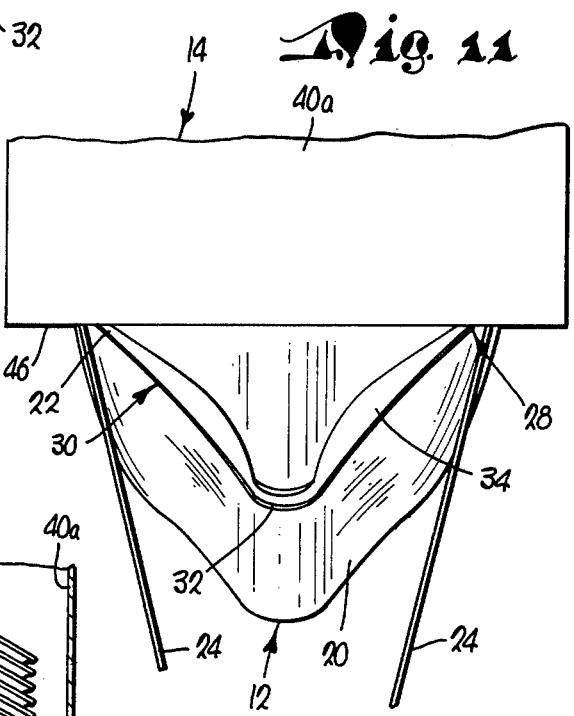
FIG. 11 is a fragmentary, front elevational view of FIG. 10.
Figure 12:
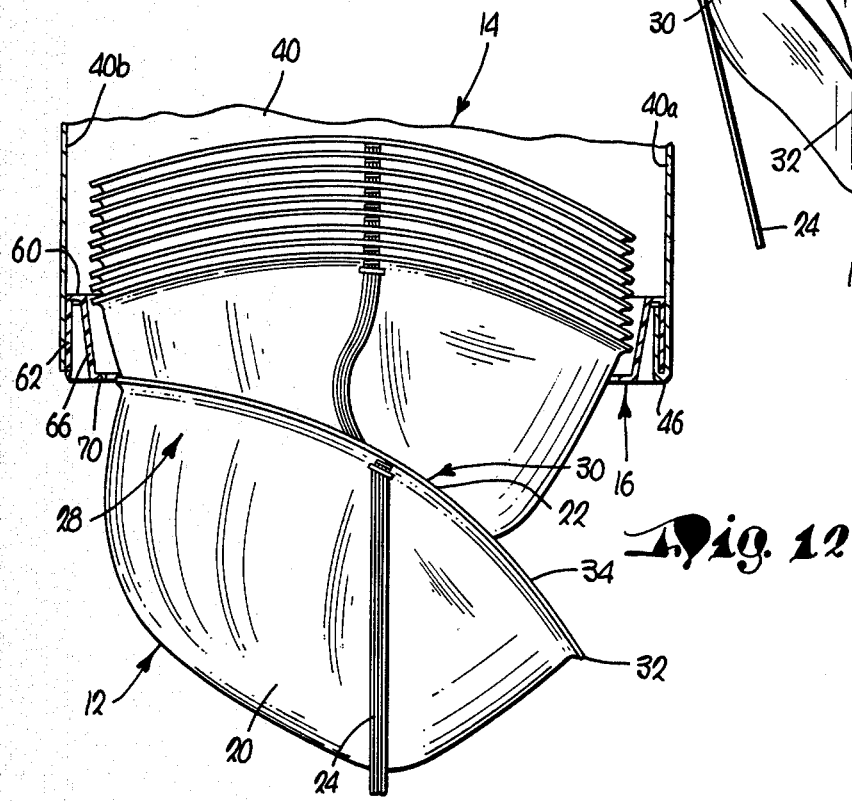
FIG. 12 is a fragmentary, elevational view in partial section similar to FIGS. 9 and 10 and illustrates the final dispensing movement a face mask.

The dispensing sequence of operation of the device 10 is best shown in FIGS. 1–2 and FIGS. 9–12. FIGS. 1 and 9 show the mask 12 in a static, beginning condition, ready for dispensing. FIGS. 2, 10, and 11 show the position of a mask 12 being dispensed. It will be appreciated that the location of the strap 24 on the mask 12, the configuration of the nose-receiving region 30 of the mask 12, and the respective configuration of the wall structure 66 and lip 70 cooperate such that a downward pull on the strap 24 causes the nose region 30 of the mask 12 to clear the retainer 16 with portions of the mouth-receiving region 28 still retained by the retainer 16. Further downward movement of the mask 12 causes the flange 22 to sequentially engage the wall structure 66 and lip 70 until the entire mask 12 finally clears the retainer 16 as shown in FIG. 12. While the first mask 12 is being dispensed, the retainer 16 effectively retains the remaining masks 12 within the container 14, whereby each succeeding mask 12 is sequentially positioned for dispensing purposes.

The use of the device 80 of the alternative embodiment illustrated in FIGS. 13–16 is virtually identical to use of the device 10 of the preferred embodiment. That is, the masks 82 are serially dispensed in response to a downward pull on either or both of the straps 88, 90. The aperture 98 is dimensioned to correlate with the cross-section of the respective face mask 82, to normally retain the mask 82 in the container 92, but to singularly dispense a mask in response to user demand.

As can be appreciated, the dispensing device of the present invention, while of a simple construction, is effective in serially dispensing face masks. Thus, the present invention is an inexpensive and convenient method for not only storing the face masks, but additionally provides ready user access heretofore unknown in the art.

We claim:

1. In combination:
    a plurality of interfitted cuplike face masks, each mask having a certain cross-section presenting a generally parabolic nose-receiving region and a generally circular mouth-receiving region, and each mask including a strap secured adjacent opposite marginal edges of said mouth-receiving portion;
    an elongated container for receiving said interfitted masks and comprising continuous sidewalls circumscribing said masks and defining a mask-receiving passageway; and
    retaining means secured transversely across said passageway and including structure defining a mask-dispensing aperture of the same general cross-sectional configuration as said mask cross-section, said masks being disposed in said passageway adjacent said retaining means with the strap of the one mask adjoining said retaining means extending through said aperture such that said masks are serially dispensed by pulling on the strap of said one mask, said one mask being removed from said container with the remaining masks being retained in said container and the strap of the next mask exposed in said aperture.

2. An invention as set forth in claim 1, said retaining means including a depending inwardly converging wall defining said aperture.

3. An invention as set forth in claim 2, said depending wall having an inwardly extending lip adjacent the distal end thereof.

4. An invention as set forth in claim 1, said retaining means including a depending wall structure having an uppermost portion secured adjacent said aperture defining structure and a lowermost, inwardly converging portion.

5. An invention as set forth in claim 4, said uppermost portion of said depending wall structure defining a cross-section approximately equal to said certain cross-section of said mask and said lowermost portion defining a cross-section proportionately less than said certain cross-section of said mask.

6. An invention as set forth in claim 5, said depending wall structure including a continuous, inwardly-extending lip adjacent said lowermost portion.

7. An invention as set forth in claim 6, said certain cross-section of said mask presenting a first, generally circular mouth-receiving region and a second, generally parabolic, nose-receiving region adjoining said first region, said second region having a smaller cross-sectional area than said first region.

8. An invention as set forth in claim 7, the perimeter of said parabolic, nose-receiving region of said mask presenting an apex, bridge-of-the-nose section and a pair of converging side sections separated by said apex section, said lip extending inwardly a greater distance in the vicinity of said side sections and a lesser distance in the vicinity of said apex section for permitting ease of removal of a respective mask.

9. An invention as set forth in claim 1, said container comprising a box being rectangular in transverse cross-section.

10. An invention as set forth in claim 1, including means for hanging said container from a hook.

11. An invention as set forth in claim 1, said retaining means presenting a generally planar engagement surface.

12. In combination:
    a stack of interfitted cuplike face masks, each mask having a certain cross-section presenting a generally parabolic nose-receiving region and a generally circular mouth-receiving region, and each mask including a strap secured adjacent opposite marginal edges of said mouth-receiving region;

an elongated container for receiving said stack of interfitted masks and defining a mask-receiving passageway; and mask retaining means carried by the container and engaging the lowermost mask of said stack to releasably retain the lowermost mask of the stack and thereby the remainder of said stack in the container, said masks being disposed in said passageway adjacent said retaining means with the strap of said one lowermost mask adjoining said retaining means extending through said aperture, said retaining means being configured such that when a user pulls downwardly on the strap of said one mask, said one mask being removed from said container initially tilts as the nose-receiving region is pulled free of the remaining stack and any retaining means therefor and then the remainder of said one mask is freed from the retaining means to assure dispensing of said masks one at a time as the remaining masks are retained in said container and the strap of the next adjacent mask extends downwardly from the container below the retaining means for grasping by a user.

* * * * *

UNITED STATES PATENT AND TRADEMARK OFFICE
CERTIFICATE OF CORRECTION

PATENT NO. : 4,550,856
DATED : November 5, 1985
INVENTOR(S) : Fred A. Ballmann and James M. Cooper It is certified that error appears in the above-identified patent and that said Letters Patent is hereby corrected as shown below:

On the title page the following should be added:

-- [73] -- Assignee: Parmelee Industries, Inc.
             Kansas City, Missouri --.

Signed and Sealed this

Eleventh Day of March 1986

[SEAL]

Attest:

Attesting Officer

DONALD J. QUIGG

Commissioner of Patents and Trademarks